United States Patent
Van Der Puy et al.

(10) Patent No.: US 6,992,224 B2
(45) Date of Patent: Jan. 31, 2006

(54) MANUFACTURE OF FLUORINATED ALCOHOLS

(75) Inventors: Michael Van Der Puy, Amherst, NY (US); Jingji Ma, West Seneca, NY (US); George J. Samuels, Willamsville, NY (US); Leonard M. Stachura, Hamburg, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 10/843,892

(22) Filed: May 12, 2004

(65) Prior Publication Data

US 2005/0256331 A1    Nov. 17, 2005

(51) Int. Cl.
C07F 5/02     (2006.01)
C07F 9/02     (2006.01)

(52) U.S. Cl. .............................................. 568/5; 568/1
(58) Field of Classification Search ................ 568/5, 568/1
See application file for complete search history.

(56) References Cited

U.S. PATENT DOCUMENTS

| | | | |
|---|---|---|---|
| 3,457,247 A * | 7/1969 | Fukui et al. ................. | 526/245 |
| 3,756,830 A | 9/1973 | Waack et al. ................. | 96/132 |
| 6,187,969 B1 | 2/2001 | Yamaguchi et al. ......... | 568/842 |
| 6,274,704 B1 | 8/2001 | Fukai et al. ................. | 530/326 |
| 6,649,719 B2 * | 11/2003 | Moore et al. ................ | 526/245 |
| 6,673,976 B1 | 1/2004 | Nair et al. ................... | 568/842 |
| 2002/0042470 A1 | 4/2002 | Moore et al. ................ | 524/544 |

OTHER PUBLICATIONS

Chambers et al., Free Radical Chemistry. Part 3, Substituent Effects in Additions of Ethers to Fluorinated Alkenes, J. Chem. Soc. Perkin Trans, 1, 1985, 2209-2213.*

LaZerte, J.D., and R. J. Koshar. "The Free-radical Catalyzed Addition of Alcohols and Aldehydes to Perfluoroolefins." Fluorine Symposium, 124$^{th}$ Meeting of the American Chemical Society. Chicago, IL, 1953, PP. 910-914.

Chambers, Richard D., Brian Grievson, and Noel M. Kelly. "Free Radical Chemistry. Part 3. Substituent Effects in Additions of Ethers to Fluorinated Alkenes." Journal of Chemical Society. Perkin Transactions, 1985, pp. 2209-2213.

Kurykin, M. A., L. S. German, L. I. Kartasheva, A.K. Pikaev. "Radiochemical addition of alcohols to perfluoro-2-alkenes." Journal of Fluorine Chemistry, vol. 77. 1996, Pp. 193-194.

Ishikawa, Nobuo, et al "Structures of the products derived from radical addition of alcohols and anhydrides to hexafluoropropene dimmer" Nippon Kagaku Kaishi, 1974 (7), 1240-4. Chemical Abstracts 81:119432e.

* cited by examiner

*Primary Examiner*—Johann Richter
*Assistant Examiner*—Chukwuma Nwaonicha
(74) *Attorney, Agent, or Firm*—Deborah M. Chess

(57) ABSTRACT

Present invention relates to a process for the manufacture of fluorinated alcohols as well as borates which are employed in the manufacture of the fluorinated alcohols. Fluorinated alcohols of the formulae $HOCHRCF(CF_3)CHFCF(CF_3)_2$ and $HOCHRCF(CF(CF_3)_2)CHFCF_3$, $HOCHRCF(CF_2CF_3)CH(CF_3)_2$ and $HOCHRC(CF_3)_2CHFCF_2CF_3$ are made by heating a mixture of a borate of the formula $(RCH_2O)_3B$, wherein R=H or a $C_1$ to $C_7$ alkyl group, with perfluoro-4-methyl-2-pentene or perfluoro-2-methyl-2-pentene and a free-radical initiator to form a mixture of borates, optionally separating the mixture of borates from any reactants, solvents, and by-products; hydrolyzing the mixture of borates to form a hydrolysis product mixture; and separating the alcohols from the hydrolysis product mixture.

27 Claims, No Drawings

MANUFACTURE OF FLUORINATED ALCOHOLS

BACKGROUND OF THE INVENTION

The present invention relates to a process for the manufacture of fluorinated alcohols as well as novel borates which are employed in the manufacture of the fluorinated alcohols.

Polyfluoroalcohols such as $RfCH_2OH$ and $RfCH_2CH_2OH$, where Rf represents a perfluoroalkyl group, are important commercial materials. Fluorinated alcohols are used as pharmaceuticals, inhalation anesthetics, herbicides, polymers, refrigerants, etchants, lubricants, heat transfer fluids, and the like. See, for example, Banks, R. E. et al "Organofluorine Chemistry, Principles and Commercial Applications" Plenum Press, New York and London, 1994, which is incorporated herein by reference. In particular, fluorinated butanols are desirable for use in the syntheses of pharmaceutical drug candidates and for use as solvents for photographic sensitizing dyes and in epoxidation and Diels-Alder reactions. See, for example, U.S. Pat. No. 3,756,830, Fluorinated alcohols: effective solvent for uncatalyzed epoxidations with aqueous hydrogen peroxide, Synnlett, vol. 2, (2001), pp. 248-(250; and Cativiela, C., et al., Fluorinated alcohols as solvents for Diels-Alder reactions of chiral acrylates Tetrahedron:Assymetry, 4(7), (1993), pp. 1613–18, each of which is incorporated herein by reference. U.S. Pat. Nos. 6,187,969 and 6,294,704, incorporated herein by reference, describe the preparation of fluoropropanols and fluorobutanols by reacting tetrafluoroethylene or hexafluoropropylene with methanol in the presence of a free radical generator and under a relatively high pressure (from about 0.2 MPa to about 1.2 MPa). However, there is rising concern over the environmental fate of the higher homologs (Rf having 6 or more carbon atoms). Alternatives to these materials include the use of lower homologs or related materials that are not fully fluorinated. The rationale for the use of fluoroalkyl groups having one or more hydrogen atoms is that a degradation pathway is made available that leads to smaller perfluorinated fragments that have little or no tendency to accumulate in living organisms (see G. G. Moore, M. A. Yandrasits, J. F. Schulz, and R. M. Flynn, PCT WO 02/16306 A2). For example, acrylates derived from a mixture of $(CF_3)_2CFCFHCF(CF_3)CH_2OH$ and $(CF_3)_2CFCF(CHFCF_3)CH_2OH$ were used to provide textile treatment formulations (A. Katsushima, I. Hisamoto, S. Fukui, and M. Nagai, see U.S. Pat. No. 3,457,247; 1969). The above-mentioned alcohols were reportedly prepared by the benzoyl peroxide catalyzed addition of methanol to $(CF_3)_2CFCF=CFCF_3$ (see N. Ishikawa, A. Nagashima, S. Hayashi, Nippon Kagaku Kaishi (1974), 7, 1240; CA (1974) 81:119432 and U.S. Pat. No. 3,457,247; 1969). However, Kurykin et al. noted that this procedure failed under the conditions reported (see M. A. Kurykin, L. S. German, L. I. Kartasheva, and A. K. Pikaev, J. Fluorine Chemistry, 77 (1996) 193). They used gamma-irradiation to catalyze the addition of methanol to the olefin either without a solvent or with methyl trifluoroacetate as the solvent. Both processes have problems for large-scale use, the latter (method of Kurykin et al.) due to the method of radical generation, and the former because the process lacks robustness. Part of the difficulty may be due to reaction non-homogeneity in the absence of a solvent, but the latter is undesirable for a variety of reasons. Chambers et al. successfully added dimethyl carbonate to hexafluoropropene using a peroxide initiator, while trimethyl borate was added to hexafluoropropene using gamma irradiation (see R. D. Chambers, B. Grievson, and N. M. Kelly, J. Chem. Soc. Perkin Trans. 1 (1985) 2209). Dimethyl carbonate and trimethyl borate may be thought of as methanol equivalents since, when the adducts are hydrolyzed, the hydrolysis products are the same as one would obtain from the addition of the hydroxymethyl radical (from methanol itself) to hexafluoropropene. It should be noted however, that in the case of hexafluoropropene, the radical addition of methanol is reliable. In contrast, it has been discovered that when $(CF_3)_2CFCF=CFCF_3$ (HFP dimer) was used instead of hexafluoropropene, poor results (poor conversion, yield, or complicated workup) were obtained, not only for methanol itself but also for methanol equivalent reagents including dimethyl carbonate and methyl t-butyl ether. Initiators included benzoyl peroxide, AIBN, t-butyl perbenzoate, and t-butyl peroxide. Surprisingly, trimethyl borate did provide a practical yield of the desired alcohol following hydrolysis of the borate adducts.

DESCRIPTION OF THE INVENTION

The invention provides a compound having one of the formulae $(RCH_2O)_2BOCHRCF(CF_3)CHFCF(CF_3)_2$; $(RCH_2O)_2BOCHRCF(CF(CF_3)_2)CHFCF_3$; $B(OCHRCF(CF_3)CHFCF(CF_3)_2)_3$; $B(OCHRCF(CF(CF_3)_2)CHFCF_3)_3$ or combinations thereof, wherein R=H or a $C_1$ to $C_7$ alkyl group.

The invention also provides a process for making a mixture of the compounds of the formulae $HOCHRCF(CF_3)CHFCF(CF_3)_2$ and $HOCHRCF(CF(CF_3)_2)CHFCF_3$ comprising a) heating a mixture of a $(RCH_2O)_3B$, wherein R=H or a $C_1$ to $C_7$ alkyl group, with perfluoro-4-methyl-2-pentene and a free-radical initiator to form a mixture of borates comprising one or more of
   $(RCH_2O)_2BOCHRCF(CF_3)CHFCF(CF_3)_2$
   $(RCH_2O)_2BOCHRCF(CF(CF_3)_2)CHFCF_3$
   $B(OCHRCF(CF_3)CHFCF(CF_3)_2)_3$ and
   $B(OCHRCF(CF(CF_3)_2)CHFCF_3)_3$ b) optionally separating the mixture of borates from any reactants, solvents, and by-products;

c) hydrolyzing the mixture of borates to form a hydrolysis product mixture comprising $HOCHRCF(CF_3)CHFCF(CF_3)_2$ and $HOCHRCF(CF(CF_3)_2)CHFCF_3$; and d) separating the $HOCHRCF(CF_3)CHFCF(CF_3)_2$ and $HOCHRCF(CF(CF_3)_2)CHFCF_3$ from the hydrolysis product mixture.

The invention further provides a process for making a mixture of the compounds of the formulae $(CF_3)_2CHCF(C_2F_5)CHROH$ and $(CF_3)_2C(CHFCF_2CF_3)CHROH$ comprising a) heating a mixture of a $(RCH_2O)_3B$, wherein R=H or a $C_1$ to $C_7$ alkyl group, with perfluoro-2-methyl-2-pentene and a free-radical initiator to form a mixture of borates comprising one or more of
   $(CF_3)_2CHCF(C_2F_5)CHROB(OCHR)_2$
   $(CF_3)_2C(CHFCF_2CF_3)CHROB(OCHR)_2$
   $((CF_3)_2CHCF(C_2F_5)CHRO)_3B$
   $((CF_3)_2C(CHFCF_2CF_3)CHRO)_3B$ b) optionally separating the mixture of borates from any reactants, solvents, and by-products;

c) hydrolyzing the mixture of borates to form a hydrolysis product mixture comprising $HOCHRCF(CF_2CF_3)CH(CF_3)_2$ and $HOCHRC(CF_3)_2CHFCF_2CF_3$; and d) separating the $HOCHRCF(CF_2CF_3)CH(CF_3)_2$ and $HOCHRC(CF_3)_2CHFCF_2CF_3$ from the hydrolysis product mixture.

Borates of the formulae $(RCH_2O)_2BOCHRCF(CF_3)CHFCF(CF_3)_2$; $(RCH_2O)_2BOCHRCF(CF(CF_3)_2)CHFCF_3$; $B(OCHRCF(CF_3)CHFCF(CF_3)_2)_3$; $B(OCHRCF(CF(CF_3)_2)CHFCF_3)_3$ or combinations thereof, wherein R=H or a $C_1$ to $C_7$ alkyl group may be prepared by heating a mixture of a $(RCH_2O)_3B$, with perfluoro-4-methyl-2-pentene or perfluoro-2-methyl-2-pentene and a free-radical initiator to form a mixture of borates.

The $(RCH_2O)_3B$ compounds that can be used include those where R is H or a saturated alkyl group with 1 to about 7 carbons. Preferably R is H or a straight chain alkyl. Most preferably, R is H or methyl.

When perfluoro-4-methyl-2-pentene is used, a mixture of borates is formed comprising one or more of
$(RCH_2O)_2BOCHRCF(CF_3)CHFCF(CF_3)_2$
$(RCH_2O)_2BOCHRCF(CF(CF_3)_2)CHFCF_3$
$B(OCHRCF(CF_3)CHFCF(CF_3)_2)_3$ and
$B(OCHRCF(CF(CF_3)_2)CHFCF_3)_3$ When perfluoro-2-methyl-2-pentene is used, a mixture of borates is formed comprising one or more of

In a preferred embodiment, the $(RCH_2O)_3B$, free radical initiator and perfluoro-4-methyl-2-pentene or perfluoro-2-methyl-2-pentene may be reacted by charging the components into a suitable reaction vessel such as an autoclave.

Free radical initiators are compounds known in the art to produce free radicals. Suitable free radical initiators non-exclusively include peroxides such as peroxides of carboxylic acids such as benzoyl peroxide and lauryl peroxide, peresters such as t-butyl perbenzoate, dialkyl peroxides such as di-t-butyl peroxide and azo initiators such as azobisisobutyronitrile (AIBN) and combinations thereof. The preferred initiators are low cost and have decomposition temperatures of at least about 50° C. The most preferred initiators are t-butyl perbenzoate, di-t-butyl peroxide, and benzoyl peroxide, and combinations thereof.

The mole ratio of perfluoro-methylpentenes to borate ester is preferably from about 1:10 to about 2:1, and more preferably from about 1:3 to about 1:1. The mole ratio of borate to initiator is preferably as high as possible, that is, from about 1:1 to about 50:1, more preferably from about 3:1 to about 25:1 and most preferably from about 5:1 to about 20:1.

The temperature of the reaction depends on the decomposition temperature of the initiator, which in turn, affects the pressure of the reaction. Initiators with a low decomposition temperature will allow lower reaction temperatures and pressures, but also represent a greater safety hazard as the decomposition temperature decreases. The temperature of the reaction may vary from about 50° C. to about 200° C., preferably from about 80° C. to about 180° C., and more preferably from about 90° C. to about 150° C. The preferred initiators are low cost and have decomposition temperatures of at least 50° C. The most preferred initiators are t-butyl perbenzoate (temperature of reaction 110° C.–120° C.), di-t-butyl peroxide (reaction temperature 120° C.–140° C.), and benzoyl peroxide (reaction temperature 100° C.–125° C.). Maximum pressure normally observed are less than 200 psi and will decrease as the reaction progresses since the volatile perfluoro-methylpentenes are converted to higher boiling materials.

Reaction times will depend on the decomposition of the initiator and the reaction temperature chosen. Usually, the reaction temperature chosen will be near the decomposition half-life for the initiator. The reaction time will then be 7–10 times the half-life in order to completely consume all the initiator. For the preferred initiators, reaction times are typically from about 10 hours to about 20 hours. With t-butyl peroxide as the initiator, for example, the reactions were conveniently accomplished using an autoclave at 130° C. for 12–20 hours. The temperature is dependent on the initiator used. Temperatures for 1-hour half-lives are known, and provide guidelines for acceptable temperature ranges. On a laboratory scale, up to 44 g of peroxide could safely be handled in a single batch (added in one portion). However, for larger-scale operations, metered addition of the peroxide over several hours should be used for safety reasons. Since trimethyl borate and perfluoropentenes are immiscible, the mixture of HFP dimer isomers, t-butyl peroxide, and trimethyl borate form a 2-phase system at room temperature. Since trimethyl borate represents a significant cost component, it is advantageous to minimize the use of the borate. Chambers et al. studied several combinations of trialkyl borates with fluoroolefins in a ratio of 2–3 moles of borate per mole of olefin. In each case, the major product, after distillation was a tris-adduct, i.e., three moles of olefin per boron. With trimethylborate (158 mmol) for example, the product from the reaction with hexafluoropropene (69 mmol) was tris-(2,2,3,4,4,4-hexafluoro-butyl) borate in 65% yield. All three of the methyl groups were utilized. This was explained by an effect of the boron atom, promoting production of a radical at the attached alkoxy site. This suggests that one could use one mole of borate with three moles of olefin. In the present case, after reacting HFP dimer with trimethyl borate, the crude reaction mixture was hydrolyzed, and fluorinated alcohol separated and distilled. Experiments showed that the largest effect on yield was the dimer to borate ratio, being greater when the ratio was low, i.e., high borate concentration. Further, the moles of product alcohol obtained, following hydrolysis and distillation, was never more than the moles of trimethyl borate added, even when the ratio of HFP dimer to borate was as high as 2:1. Thus, a second major difference is seen when HFP dimer is compared to hexafluoropropene and the fluorinated cyclic compounds used by Chambers, et al.

The reaction may optionally be conducted in the presence of solvents such as low molecular weight nitrites and esters such as acetonitrile and ethyl acetate. When a solvent is used, the amount of solvent may range from about 10% to about 60% by weight of the total mixture. Preferably, no solvent is used.

Next the resulting mixture of borates may optionally be separated from any residual reactants, solvents, and by-products. This may be done by well known separation techniques such as distillation. The conditions of such separation may be easily determined by those skilled in the art, depending on the selection of reactants and desired end products. Residual $(RCH_2O)_3B$ may then be recycled back to step a).

Distillation of the crude reaction mixture at atmospheric pressure to remove volatiles may be followed by vacuum distillation to recover and identify the borate intermediate. $^1H$ NMR revealed that the latter contained only a minor amount of methoxy groups, but had 2 multiplets in a 2:1 ratio. Mass spectral analysis indicated a molecular weight over 1000. Thus the distilled product appears to be mainly the tris-adduct. It is believed that while the radical reaction produces only the mono-adduct $((CH_3O)_2BOCH_2CF(CF_3)CHFCF(CF_3)_2$ and $(CH_3O)_2BOCH_2CF(CF(CF_3)_2)CHFCF_3)$, during distillation process, during which volatile borates are removed, an equilibrium process occurs. This process generates, from the initial mono-adduct, both trimethylborate and the tris-adducts, B(OCH$_2$CF(CF$_3$)CHFCF(CF$_3$)$_2$)$_3$ and B(OCH$_2$CF(CF(CF$_3$)$_2$)CHFCF$_3$)$_3$. Thus distilling the product prior to hydrolysis has the effect of utilizing all three methyl groups of trimethylborate. The recovered trimethylborate may be recycled. Using a mole ratio of borate to dimer of about two, the amount of peroxide added was lowered in successive experiments to determine its effect on dimer consumption. It was found that dimer conversion decreased to 93% as the initial dimer to peroxide mole ratio increased from 3.1 to 5.6. At a ratio of 9.5 however, the dimer conversion was only 80%. Offsetting the lower conversion of dimer was a modest increase in reaction yield, based on un-recovered dimer, from 68 to 76%. Thus, there are opposing effects as the dimer to peroxide ratio is increased. Adding the peroxide incrementally or adding it slowly over time produced the best overall results.

A dramatic difference is seen in the behavior of methanol verses trimethylborate in the reaction with perfluoro-2-methyl-2-pentene instead of perfluoro-4-methyl-2-pentene. In the reaction of methanol with perfluoro-2-methyl-2-pentene, the addition of HOCH$_2$ radicals to the olefin is only a minor reaction. The major reaction product is the addition of methanol to give the corresponding methyl ether, (CH$_3$OCF(C$_2$F$_5$)CH(CF$_3$)$_2$). The use of trimethyl borate eliminates this undesirable side reaction.

Next the mixture of borates is hydrolyzed to form a hydrolysis product mixture. The borate esters are easily hydrolyzed by contact with water at a temperature of from about 0° C. to about 100° C., preferably from about 25° C. to about 50° C. Since boric acid is a co-product it is convenient to add a base such as NaOH or Na$_2$CO$_3$ to solubilize the boric acid and facilitate separation from the liquid product alcohols.

Next the resulting alcohols are separated from the hydrolysis product mixture. This may be done by well known separation techniques such as distillation. The conditions of such separation may be easily determined by those skilled in the art, depending on the selection of reactants and desired end products.

The following non-limiting examples serve to illustrate the invention. It will be appreciated that variations in proportions will be apparent to those skilled in the art and are within the scope of the present invention.

EXAMPLE 1

Preparation Using t-butyl perbenzoate and Trimethylborate

A 450-mL autoclave was evacuated and charged with 82.0 g (0.27 mol) perfluoro-4-methyl-2-pentene, 19.5 g (0.1 mol) t-butyl perbenzoate and 29.3 g (0.28 mol) trimethylborate. The mixture was stirred (300 rpm) and heated to 120° C. for 21 hours. A modest exotherm of about 8° occurred when the temperature reached approximately 115° C. The maximum observed pressure was 108 psig. After cooling the autoclave in an ice bath, the contents were removed and distilled at atmospheric pressure. The first distillation cut boiled at 32–48° C. (mainly 35° C.). The overhead condensate consisted of two phases. Only the lower layer was removed (11.5 g), which was subsequently washed with water to give 9.4 g of perfluoro-4-methyl-2-pentene, indicating a conversion of 89%. The second distillation cut (17.4 g) boiled at 48–60° C. (mainly 53° C.). The pot residue (104.3 g) was then hydrolyzed in water containing a little sodium bicarbonate. The lower layer was separated, dried, and distilled at 70 mm Hg to give 32.8 g of the desired alcohols (a mixture of isomers, i.e., the product mixture containing HOCH$_2$CF(CF$_3$)CHFCF(CF$_3$)$_2$ or 2,3,4,5,5,5-hexafluoro-2,4-bis-trifluoromethyl-pentan-1-ol and HOCH$_2$CF(CF(CF$_3$)$_2$)CHFCF$_3$ or 2,3,4,4,4-pentafluoro-2-(1,2,2,2-tetrafluoroethyl)-3-trifluoromethyl-butan-1-ol), bp 77–81° C. (41% yield based on un-recovered perfluoro-4-methyl-2-pentene).

EXAMPLE 2

Preparation Using di-t-butyl peroxide and Trimethylborate

In a manner similar to that of Example 1, 162.7 g (0.54 mol) perfluoro-4-methyl-2-pentene, 14.1 g (0.096 mol) di-t-butyl peroxide, and 29.6 g (0.285 mol) trimethyl borate were stirred and heated to 130° C. for 21 hours. The maximum observed pressure was 106 psig. Workup as described in Example 1 gave 30.0 g unreacted perfluoro-4-methyl-2-pentene and 78.5 g of the same desired fluoroalcohols as in Example 1 (54% yield based on un-recovered olefin. The GC purity was 92%, which was increased to at least 95% by re-distillation at atmospheric pressure, bp 140–143° C. $^{19}$F NMR (CDCl$_3$/CFCl$_3$): isomer A, CF$_3$ fluorines at −72.6, −75.9, and −76.6 ppm and CF fluorines at −186.9, −188.1, and −210.3 ppm; isomer B, CF$_3$ fluorines at −72.6, −75.2, and −76.9 ppm and CF fluorines at −185.7, −190.0, and −214.3 ppm. $^1$H NMR: OH, δ 2.2; CH$_2$, multiplets at δ 4.16 and 4.22; CHF, ddd at 5.68 (J=7.2, 22.6, and 42.7 Hz); dddd at δ 5.51 (J=0.8, 10.1, 15.0, and 43.0 Hz).

EXAMPLE 3

Isolation of the Intermediate Fluorinated Borate Ester

In a manner similar to Example 2, 100 mL of perfluoro-4-methyl-2-pentene, 62 mL of trimethylborate and 17.7 g of di-t-butyl peroxide were heated to 130° C. for 18 hours. The crude reaction mixture was distilled without hydrolysis. The fraction boiling at 120° C. at 90 mm Hg weighed 87.8 grams. $^1$H NMR: δ 5.9–6.3 (m, 24.9% of integrated area), δ 4–4.7 (m, 57.7% of integrated area) and δ 1.33 (s, 17.4% of integrated area). $^{19}$F NMR: CF$_3$ fluorines were at −71.7 to −76.2 ppm while CF fluorines were at −184.2 to −212.9 ppm. $^{11}$B NMR showed a broad peak at 4 ppm relative to NaBF$_4$. By GCMS analysis, this was primarily a mixture of B(OCH$_2$CF(CF$_3$)CHFCF(CF$_3$)$_2$)$_3$ or tris(2,3,4,5,5,5-hexafluoro-2,4-bis-trifluoromethyl-pentyl) borate and B(OCH$_2$CF(CF(CF$_3$)$_2$)CHFCF$_3$)$_3$ or tris(2,3,4,4,4-pentafluoro-2-(1,2,2,2-tetrafluoroethyl)-3-trifluoromethyl-butyl) borate. Some borates bearing a methoxy group were still present, however, as indicated by the singlet in the NMR spectrum at 1.33 ppm.

EXAMPLE 4

Use of Excess Trimethyl Borate and Recovery of Trimethyl Borate

A 1-liter autoclave was charged with 240 mL (225 g, 2.12 mol) trimethylborate, 170 mL (279 g, 0.93 mol) perfluoro-4-methyl-2-pentene, and 44 g (0.30 mol) t-butyl peroxide. The contents were then heated to 126–130° C. for 22 hours. The maximum pressure was 120 psig. Distillation was conducted to remove volatile materials at atmospheric pressure. The trimethyl borate fraction boiling at 67–68.5° C. (89.3 g) was 92% pure by GC. The cooled pot residue was hydrolyzed to give 277 g crude alcohol. It was dried and distilled at 76–77 mm Hg to give 210 g (0.63 mol, 68% yield) of the desired alcohol isomers (as in Example 1; better than 95% purity by GC analysis) in approximately equal amounts, bp 78–82° C. The yield is substantially higher compared to Example 2 where the mole ratio of perfluoro-4-methyl-2-pentene to trimethylborate was 1.9 rather than 0.44 used here.

EXAMPLE 5

Using a 0.91 Mole Ratio of perfluoro-4-methyl-2-pentene to Trimethylborate

A 1-liter autoclave was charged with 159 g (1.5 mol) trimethylborate, 410 g (1.36 mol) perfluoro-4-methyl-2-pentene, and 44 g (0.30 mol) t-butyl peroxide. The contents were then heated to 126–130° C. for 15.5 hours. The maximum pressure was 120 psig. Distillation was conducted to remove volatile materials at atmospheric pressure (170 g, bp to 90° C.). The cooled pot residue (346 g) was treated with 300 mL water and enough sodium bicarbonate to dissolve the solid (boric acid). The lower layer was washed twice with 500 mL water, then dried ($Na_2SO_4$) and distilled. The yield of the mixture of alcohols (same as in Example 1) boiling at 79–86° C. at 78–79 mm Hg, was 248 g (55%).

EXAMPLE 6

In a manner similar to Example 5, 280 g of perfluoro-4-methyl-2-pentene, 228 g of trimethylborate and 40 g of t-butyl peroxide were heated and stirred under autogenous pressure. The yield of the fluorinated alcohols (same as in Example 1) was 72%.

EXAMPLE 7

In a manner similar to Example 5, 279 g of perfluoro-4-methyl-2-pentene, 228 g of trimethylborate and 30 g of t-butyl peroxide were heated and stirred under autogenous pressure. The recovered dimer weighed 9 g and the yield of fluorinated alcohols (same as in Example 1), based on unrecovered dimer, was 72%.

EXAMPLE 8

In a manner similar to Example 5, 278 g of perfluoro-4-methyl-2-pentene, 221 g of trimethylborate and 20 g of t-butyl peroxide were heated and stirred under autogenous pressure. The recovered dimer weighed 9 g and the yield of the fluorinated alcohols (same as in Example 1), based on unrecovered dimer, was 79%.

EXAMPLE 9

In a manner similar to Example 5, 286 g of perfluoro-4-methyl-2-pentene, 223 g of trimethylborate and 15 g of t-butyl peroxide were heated and stirred under autogenous pressure. The recovered dimer weighed 56 g and the yield of the fluorinated alcohols (same as in Example 1), based on unrecovered dimer, was 76%.

EXAMPLE 10

Example 9 was repeated (284 g of perfluoro-4-methyl-2-pentene, 224 g of trimethylborate) except that a total of 15.8 g of t-butyl peroxide was added in four approximately equal increments at 0, 1, 3, and 5 hours. The recovered dimer weighed 28 g and the yield of the fluorinated alcohols (same as in Example 1), based on unrecovered dimer, was 82%.

Thus the conversion and yield both increased when the initiator was added incrementally rather than all at once at the beginning of the reaction.

EXAMPLE 11

This Example is similar to Example 10, except that 16.5 g of t-butyl peroxide was pumped into a mixture of 220 g trimethyl borate, and 284 g HFP dimer over 8 hours. The recovered dimer weighed 12 g (96% conversion of dimer). The yield of the fluorinated alcohols (same as in Example 1) was 234 g (78% yield).

Examples 12–16 are comparative Examples using alternative reagents

EXAMPLE 12 (COMPARATIVE)

A mixture of 52.6 g methyl t-butyl ether, 32.8 g perfluoro-4-methyl-2-pentene, and 2 g t-butyl peroxide was heated in an autoclave to 140° C. for 18 hours. After two distillations, 9.1 g of material (bp 81-(83° C. at 55 mm Hg) of only 76% purity by GC was obtained. The pot residue of a few grams was 91% pure. NMR analysis was consistent with a mixture of $(CH_3)_3COCH_2CF(CF_3)CHFCF(CF_3)_2$ and $(CH_3)_3COCH_2CF(CHFCF_3)CF(CF_3)_2$. The ratio of isomers was approximately 2:1. For the isomer in larger amount, $^1H$ NMR: δ 5.67 (CHF), 3.86 ($CH_2$), and 1.18 (($CH_3)_3C$); $^{19}F$ NMR: $CF_3$ groups at −72.6, −75.6, and −77.4; the CF groups at −185.9, −189.8, and −215.0 ppm. For the isomer in smaller amount, $^1H$ NMR: δ 5.50 (CHF), 3.74 ($CH_2$), and 1.20 (($CH_3)_3C$); $^{19}F$ NMR: $CF_3$ groups at −72.6, −74.3, and −76.8; CF groups at −186.5, −187.6, and −212.4 ppm.

EXAMPLE 13 (COMPARATIVE)

A mixture of 15.2 g dimethylcarbonate, 122.7 g of perfluoro-4-methyl-2-pentene, and 2.2 grams of t-butyl peroxide was heated in an autoclave to 140–148° C. for 16 hours. Although peroxide was absent, very little reaction of perfluoro-4-methyl-2-pentene had occurred.

EXAMPLE 14 (COMPARATIVE)

A mixture of 10.6 g of dimethylcarbonate, 122.1 g of perfluoro-4-methyl-2-pentene, and 1.5 g of benzoyl peroxide was heated in an autoclave to 93-(107° C. for 1.5 h followed by 1 hour at 110–120° C. There was no reaction as determined by GC.

EXAMPLE 15 (COMPARATIVE)

Similarly no reaction occurred when a mixture of 10.2 g of dimethylcarbonate, 119.7 g of perfluoro-4-methyl-2-pentene, and 1.24 g of AIBN was heated in an autoclave to 90-(94° C. for 19 hours.

EXAMPLE 16 (COMPARATIVE)

A 1-liter monel autoclave was charged with 300 g of methanol, 90 g of perfluoro-4-methyl-2-pentene, and 5 g of t-butyl peroxide. The contents were heated to 130° C. for 18 hours, then cooled and the two layers separated. The lower layer, after washing with water, was recovered perfluoro-4-methyl-2-pentene (71.5 g) of 99.3% purity. The upper layer contained 8.9 g of the fluorinated alcohols (same as in Example 1) by GC analysis. Distillation of the upper layer gave, after washing with water, an additional 2 g of perfluoro-4-methyl-2-pentene. The conversion of olefin was therefore 18%. Some corrosion of the inner autoclave parts was evident by a copper-like appearance on the exposed surfaces. This corrosion was not evident in alcohol preparations using trimethyl borate instead of methanol.

EXAMPLE 17

Reaction of Methanol with the "Thermodynamic" HFP Dimer, perfluoro-2-methyl-2-pentene Into a 300-mL autoclave was charged 1.0 g of benzoyl peroxide, 75 g of perfluoro-2-methyl-2-pentene, and 35 g of methanol under conditions to maintain an oxygen-free environment. The contents were then heated to 98–100° C. for 10 hours. The cooled reaction mixture was diluted with 250 mL of water. The organic phase was separated, washed with water, and dried to give 70 g of crude product. Distillation provided 34.5 g boiling at 90–115° C., which consisted primarily mainly of the methyl ether, $CH_3OCF(C_2F_5)CH(CF_3)_2$, and the corresponding olefin produced by its dehydrofluorination, and 12.5 g, bp 140–150° C., consisting primarily of the alcohol, $HOCH_2CF(C_2F_5)CH(CF_3)_2$. Thus, the main product under these conditions is not the alcohol, but the methyl ether. This is in contrast to the results for the addition of methanol to hexafluoropropene under radical conditions, where the corresponding alcohol is produced in good yield.

EXAMPLE 18

Reaction of Trimethyl Borate with the "Thermodynamic" HFP Dimer, perfluoro-2-methyl-2-pentene A 300-mL autoclave was charged with 15.1 g t-butyl peroxide, 280.4 g of perfluoro-2-methyl-2-pentene, and 222.7 g of trimethyl borate under conditions to maintain an oxygen-free environment. The contents were heated to 130° C., at which point an exotherm occurred to a maximum of 150° C., which subsided in about 0.5 h. The temperature was then held at 130° C. (total reaction time 22.5 h). The crude reaction mixture (one phase) was distilled at atmospheric pressure to remove 175.1 g of volatiles (bp up to 80° C.), which did not contain unreacted HFP dimer. The pot residue was treated with 600 mL of water containing 63.5 g of sodium bicarbonate. The organic layer (290 g) was dried and distilled to give 240 g of 2 products in a ratio of 4.24 to 1 (96% of the total distillate), bp 77-(83° C. at 73 torr. By NMR, the major isomer was identified as $(CF_3)_2CHCF(C_2F_5)CH_2OH$. $^1H$ NMR: δ 4.2 (m, $CH_2$ and CH), 2.6 (t, OH); $^{19}F$ NMR: –60.5 (dm, 6F), –81.1 (d, 3F), –119.4 (AB quartet, 2F), and –177.2 (1F) ppm. The minor isomer was identified as $(CF_3)_2C(CH_2OH)CHFCF_2CF_3$. $^1H$ NMR: δ 5.7 (dd, CHF), 4.2 ($CH_2$), and 2.3 (t, OH). $^{19}F$ NMR: –65.7 (6F, $C(CF_3)_2$), –84.8 (d, 3F, $CF_3$), –127.5 (AB quartet, 2F, $CF_2$), and –212.3 (m, 1F) ppm.

Thus the main product from the reaction of methanol and of trimethyl borate with perfluoro-2-methyl-2-pentene is not the same, which demonstrates the difference in behavior of hexafluoropropene dimers relative to hexafluoropropene itself.

EXAMPLE 19

Reaction of Trimethylborate with Trifluoropropene

An autoclave was charged with 48 g of trimethylborate, 1.5 g of t-butyl peroxide, and 20.5 g of $CF_3CH=CH_2$. The contents were heated to 130° C. for 18 hours. About 2 grams of gas was vented off after the contents had cooled to room temperature. The remaining liquid portion was distilled to recover 41 g of unreacted trimethylborate. By GC analysis, the pot residue (8.8 g) was very complex. The desired product, $CF_3CH_2CH_2CH_2OH$, was not more than 5% of this mixture. Thus the scope of the reaction with trimethylborate, as a synthetic route to fluorinated alcohols, does not extend to all fluorinated olefins.

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above and all equivalents thereto.

What is claimed is:

1. A compound having one of the formulae $(RCH_2O)_2BOCHRCF(CF_3)CHFCF(CF_3)_2$; $(RCH_2O)_2BOCHRCF(CF(CF_3)_2)CHFCF_3$; $B(OCHRCF(CF_3)CHFCF(CF_3)_2)_3$; $B(OCHRCF(CF(CF_3)_2)CHFCF_3)_3$ or mixtures thereof, wherein R=H or a $C_1$ to $C_7$ alkyl group.

2. The compound according to claim 1 having the formula $(RCH_2O)_2BOCHRCF(CF_3)CHFCF(CF_3)_2$, wherein R H or a $C_1$ to $C_7$ alkyl group.

3. The compound according to claim 1 having the formula $(RCH_2O)_2BOCHRCF(CF(CF_3)_2)CHFCF_3$, wherein R=H or a $C_1$ to $C_7$ alkyl group.

4. The compound according to claim 1 having the formula $B(OCHRCF(CF_3)CHFCF(CF_3)_2)_3$, wherein R=H or a $C_1$ to $C_7$ alkyl group.

5. The compound according to claim 1 having the formula $B(OCHRCF(CF(CF_3)_2)CHFCF_3)_3$, wherein R=H or a $C_1$ to $C_7$ alkyl group.

6. The compound according to claim 1 having the formula $(Ch_3O)_2BOCH_2CF(CF_3)CHFCF(CF_3)_2$.

7. The compound according to claim 1 having the formula $(CH_3O)_2BOCH_2CF(CF(CF_3)_2)CHFCF_3$.

8. The compound according to claim 1 having the formula $B(OCH_2CF(CF_3)CHFCF(CF_3)_2)_3$.

9. The compound according to claim 1 having the formula $B(OCH_2CF(CF(CF_3)_2)CHFCF_3)_3$.

10. The compound according to claim 1 comprising a combination of more than one of $(CH_3O)_2BOCH_2CF(CF_3)CHFCF(CF_3)_2$; $(CH_3O)_2BOCH_2CF(CF(CF_3)_2)CHFCF_3$; $B(OCH_2CF(CF_3)CHFCF(CF_3)_2)_3$; $B(OCH_2CF(CF(CF_3)_2)CHFCF_3)_3$.

11. A composition comprising a compound according to claim 1.

12. A process for making a mixture of the compounds of the formulae $HOCHRCF(CF_3)CHFCF(CF_3)_2$ and $HOCHRCF(CF(CF_3)_2)CHFCF_3$ comprising
   a) heating a mixture of a $(RCH_2O)_3B$, wherein R=H or a $C_1$ to $C_7$ alkyl group, with perfluoro-4-methyl-2-pentene and a free-radical initiator to form a mixture of borates comprising one or more of
      $(RCH_2O)_2BOCHRCF(CF_3)CHFCF(CF_3)_2$
      $(RCH_2O)_2BOCHRCF(CF(CF_3)_2)CHFCF_3$
      $B(OCHRCF(CF_3)CHFCF(CF_3)_2)_3$ and
      $B(OCHRCF(CF(CF_3)_2)CHFCF_3)_3$
   b) optionally separating the mixture of borates from any reactants, solvents, and by-products;
   c) hydrolyzing the mixture of borates to form a hydrolysis product mixture comprising $HOCHRCF(CF_3)CHFCF(CF_3)_2$ and $HOCHRCF(CF(CF_3)_2)CHFCF_3$; and d) separating the HOCHRCF(CF$_3$)CHFCF(CF$_3$)$_2$ and HOCHRCF(CF(CF$_3$)$_2$)CHFCF$_3$ from the hydrolysis product mixture.

13. The process of claim 12 wherein the borates of step (a) comprises one or more of
(CH$_3$O)$_2$BOCH$_2$CF(CF$_3$)CHFCF(CF$_3$)$_2$
(CH$_3$O)$_2$BOCH$_2$CF(CF(CF$_3$)$_2$)CHFCF$_3$
B(OCH$_2$CF(CF$_3$)CHFCF(CF$_3$)$_2$)$_3$ and
B(OCH$_2$CF(CF(CF$_3$)$_2$)CHFCF$_3$)$_3$
and the hydrolysis product mixture of step (c) comprises HOCH$_2$CF(CF$_3$)CHFCF(CF$_3$)$_2$ and HOCH$_2$CF(CF(CF$_3$)$_2$)CHFCF$_3$.

14. The process of claim 12 wherein the (RCH$_2$O)$_3$B comprises (CH$_3$O)$_3$B.

15. The process of claim 12 wherein the free radical initiator comprises a peroxide.

16. The process of claim 12 wherein the free radical initiator comprises benzoyl peroxide, t-butyl peroxide, t-butyl perbenzoate, di-t-butyl peroxide, or mixtures thereof.

17. The process of claim 12 wherein the result of step b) comprises a (RCH$_2$O)$_3$B which is then recycled to step a).

18. The process of claim 12 wherein the step c) hydrolyzing is conducted with aqueous sodium bicarbonate.

19. The process of claim 12 wherein the step d) separating is conducted with distillation.

20. A process for making a mixture of the compounds of the formulae (CF$_3$)$_2$CHCF(C$_2$F$_5$)CHROH and (CF$_3$)$_2$C(CHFCF$_2$CF$_3$)CHROH comprising
a) heating a mixture of a (RCH$_2$O)$_3$B, wherein R=H or a C$_1$ to C$_7$ alkyl group, with perfluoro-2-methyl-2-pentene and a free-radical initiator to form a mixture of borates comprising one or more of
(CF$_3$)$_2$CHCF(C$_2$F$_5$)CHROB(OCHR)$_2$
(CF$_3$)$_2$C(CHFCF$_2$CF$_3$)CHROB(OCHR)$_2$
((CF$_3$)$_2$CHCF(C$_2$F$_5$)CHRO)$_3$B
((CF$_3$)$_2$C(CHFCF$_2$CF$_3$)CHRO)$_3$B b) optionally separating the mixture of borates from any reactants, solvents, and by-products;

c) hydrolyzing the mixture of borates to form a hydrolysis product mixture comprising HOCHRCF(CF$_2$CF$_3$)CH(CF$_3$)$_2$ and HOCHRC(CF$_3$)$_2$CHFCF$_2$CF$_3$; and d) separating the HOCHRCF(CF$_2$CF$_3$)CH(CF$_3$)$_2$ and HOCHRC(CF$_3$)$_2$CHFCF$_2$CF$_3$ from the hydrolysis product mixture.

21. The process of claim 20 wherein the borates of step (a) comprises one or more of
(CF$_3$)$_2$CHCF(C$_2$F$_5$)CH$_2$OB(OCH$_3$)$_2$
(CF$_3$)$_2$C(CHFCF$_2$CF$_3$)CH$_2$OB(OCH$_3$)$_2$
((CF$_3$)$_2$CHCF(C$_2$F$_5$)CH$_2$O)$_3$B
((CF$_3$)$_2$C(CHFCF$_2$CF$_3$)CH$_2$O)$_3$B
and the hydrolysis product mixture of step (c) comprises HOCH$_2$CF(CF$_2$CF$_3$)CH(CF$_3$)$_2$ and HOCH$_2$C(CF$_3$)$_2$CHFCF$_2$CF$_3$.

22. The process of claim 20 wherein the (RCH$_2$O)$_3$B comprises (CH$_3$O)$_3$B.

23. The process of claim 20 wherein the free radical initiator comprises a peroxide.

24. The process of claim 20 wherein the free radical initiator comprises benzoyl peroxide, t-butyl peroxide, t-butyl perbenzoate, di-t-butyl peroxide, or mixtures thereof.

25. The process of claim 20 wherein the result of step b) comprises (CH$_3$O)$_3$B which is then recycled to step a).

26. The process of claim 20 wherein the step c) hydrolyzing is conducted with aqueous sodium bicarbonate.

27. The process of claim 20 wherein the step d) separating is conducted with distillation.

\* \* \* \* \*